United States Patent [19]

Chen

[11] 4,164,564

[45] Aug. 14, 1979

[54] OINTMENT AND CREAM BASES CAPABLE OF WITHSTANDING ELEVATED TEMPERATURES

[75] Inventor: James L. Chen, East Brunswick, N.J.

[73] Assignee: E. R. Squibb & Sons, Inc., Princeton, N.J.

[21] Appl. No.: 930,848

[22] Filed: Aug. 4, 1978

Related U.S. Application Data

[63] Continuation-in-part of Ser. No. 753,968, Dec. 23, 1976, abandoned.

[51] Int. Cl.$^2$ .................... A61K 31/745; A61K 9/10; A61K 9/00; A61K 47/00
[52] U.S. Cl. .................................. 424/83; 424/170; 424/172; 424/358; 424/365; 424/DIG. 5; 424/153; 424/181; 424/62; 424/331; 424/289; 424/324; 424/258
[58] Field of Search ............... 424/DIG. 5, 365, 172, 424/170, 153, 83, 358

[56] References Cited

U.S. PATENT DOCUMENTS

| | | | |
|---|---|---|---|
| 2,617,754 | 11/1952 | Neely | 424/DIG. 5 |
| 2,627,938 | 2/1953 | Frohmader et al. | 424/358 |
| 2,628,187 | 2/1953 | Frohmader et al. | 424/358 |
| 3,957,969 | 5/1976 | Fujiyama et al. | 424/DIG. 5 |
| 4,032,588 | 6/1977 | Tomita et al. | 424/DIG. 5 |

FOREIGN PATENT DOCUMENTS 629433 10/1961 Canada .................................. 424/365
884688 12/1961 United Kingdom .

OTHER PUBLICATIONS

Chem. Abstracts, vol. 80: items 6778h, 19396g, 47485d (1974), vol. 82: item 21725y (1975); vol. 83: items 48084w & 116041g (1975), vol. 84: items 181886w (1976).
Cosmetics & Perfumery, vol. 89, Jul. 1974, pp. 45–48 & vol. 90, Sep. 1975, pp. 55–57.

*Primary Examiner*—Donald B. Moyer
*Attorney, Agent, or Firm*—Lawrence S. Levinson; Burton Rodney

[57] ABSTRACT

Non-rancid absorption ointment bases are provided which have a high capacity for water absorbability and are capable of withstanding elevated temperatures and are formed of gelled mineral oil and an ester of non-rancid isostearic acid such as sorbitan triisostearate, sorbitan sesqui-isostearate, or triglyceryl diisostearate, or an ether of non-rancid isostearyl alcohol such as polyethylene glycol diisostearate.

Water-in-oil non-rancid creams resulting from the incorporating of water or medicinal solutions into the above bases are also provided and are capable of withstanding elevated temperatures.

The above ointments and creams may be employed as carriers for medicaments such as antibiotics, anti-bacterial agents, antihistamines, anti-fungal agents and the like.

11 Claims, No Drawings

OINTMENT AND CREAM BASES CAPABLE OF WITHSTANDING ELEVATED TEMPERATURES

REFERENCE TO OTHER APPLICATIONS

This application is a continuation-in-part of application Ser. No. 753,968 filed Dec. 23, 1976 now abandoned.

The present invention relates to ointment bases which are capable of absorbing large quantities of water, and water-in-oil creams resulting from the incorporation of water into such bases; the ointment bases and creams can withstand elevated temperatures of 50°–80° C. or higher and do not become rancid on storage.

U.S. Pat. Nos. 2,627,938 and 2,628,187 disclose mineral oil vehicles prepared by dissolving a thickening or gelling agent in the mineral oil at elevated temperatures and then gelling by so-called "shock cooling." Gelled mineral oil prepared as described above and containing sorbitan oleate as a water-in-oil emulsifier can absorb two to three times its weight in water. However, unfortunately, it has been found that the above vehicle is not stable and becomes rancid on storage at room temperature and especially at elevated temperatures such as 40° C. or higher.

It has been found that the above rancidity problem may be overcome by the use of "saturated" non-rancid isostearate esters or isostearyl ethers as described hereinafter in preparing the gelled mineral oil type of high melting or softening absorption bases which melt or soften above 50° C. Furthermore, the resulting carriers or vehicles in the form of creams or ointments will be physically stable in the temperature range of from 5°–80° C. and yet do not become rancid at elevated temperatures above 50° C. and even to 80° C. or higher depending upon the amount and molecular weight of the particular gelling agent used in the composition. The absorption base or ointment is prepared by incorporating at room temperature in the gelled semi-solid oleaginous vehicle a water-in-oil emulsifier which is an oily liquid at room temperature and contains no unsaturated fatty acid moiety in its molecule. It is important that the emulsifier be a liquid at room temperature or slightly higher and be immiscible in the oily medium without applying heat since heating of the gelled ointment will cause excessive oil separation or syneresis.

The liquid water-in-oil emulsifier will comprise an ester of isostearic acid containing ½ to 3 units of isostearate and having a hydrophilic-lipophilic balance (HLB) of from 1 to 7 or an ether of isostearyl alcohol having an HLB of 1 to 7. The emulsifier will be employed in amounts greater than 0.5% by weight of the total vehicle composition and preferably within the range of from about 1 to about 30% by weight of the total vehicle composition.

Examples of emulsifiers suitable for use herein include sorbitan sesqui-isostearate, triglyceryl di-isostearate, sorbitan tri-isostearate, polyethylene glycol (2) isostearyl ether, polyethylene glycol (2) di-isostearyl ether, polypropylene glycol (2) isostearyl ether, polypropylene (2) di-isostearyl ether as well as mixtures of the above.

The bases or vehicles which may be modified as described above, in accordance with the present invention, may be any of those described in U.S. Pat. Nos. 2,627,938, 2,628,187, 2,628,205, 3,029,188 and 3,733,403 (all of which are incorporated herein by reference). Such bases will generally include mineral oils (as described in U.S. Pat. No. 3,029,188) containing a thickening agent.

The oils which may be used and which are embraced within the term "mineral oil" as used herein are the oils which are liquid at any temperature in the range from 0° C. to 60° C. and which are essentially hydrocarbons occurring in mineral oil, their distillates and their cracked or polymerized derivatives, an example of the last being polybutene which includes the liquid lower and semi-solid higher polymers of butylene and its isomers. The mineral oil may be of any desired character or viscosity, from one which is a thin liquid to one which is so thick that it does not flow readily at ordinary temperature (20° C.).

Thickening (gelling) agents utilizable for dispersion in the mineral oil include high melting waxes, such as, inter alia natural or synthetic paraffin waxes, amorphous wax (e.g., microcrystalline wax), ozokerite, high melting point waxes melting at 137°–139° C., animal waxes (e.g., beeswax), vegetable waxes (e.g., castor wax and carnauba wax), and hydrocarbon polymers (e.g., polymers of ethylene having an average molecular weight varying from 3,500 to 26,000 and solid polyisobutylene of a higher molecular weight), methylpentene polymers such as TPX grade R methylpentene polymers supplied by I.C.I. (Organics Inc.) and very high molecular weight fatty acids of $C_{29}$ and higher and melting at 67°–73° C. (Emery 865-A, Emery Ind.) and/or polyamide complex of hydroxystearate.

Other oil liquid bases or vehicles which can be employed herein include, but are not limited to, emollients such as isopropyl palmitate, isopropyl myristate, diethylsebacate, diethyl lactate, 2-ethylhexyl isononanoate 2-ethylhexyl pelargonate, isostearyl alcohol, or isostearic acid gelled or thickened with any of the aforementioned thickening agents as well as petrolatum, high molecular weight paraffin waxes or mono- and diglycerides of fatty acids gelled with very high molecular weight fatty acids.

It will also be noted that emollients such as isopropyl myristate may be added to overcome the oily feel of the mineral oil.

The absorption ointments of the invention can form water-in-oil emulsions by simply mixing water or aqueous solution or suspension of medicinal agents with the ointment at room temperature.

A preservative may also be added to the bases of the invention. Such preservatives which may be added, depending upon the pharmacologically active material utilized when said base is intended for use as a vehicle include, inter alia, methyl paraben, propylparaben, esters of p-hydroxybenzoic acid, sorbic acid, volatile oils (e.g., peppermint, wintergreen, cinnamon), benzoic acid and its salts.

If it is desired to vary the fragrance, taste and/or color features of the bases of the invention, this may be done by the addition of essential oils, synthetic aromatics or other similar flavoring materials (for taste) and, suitable oil-soluble Food Drug and Cosmetic or Drug and Cosmetic dyes or inert pigments (for color).

Examples of preferred ointment bases in accordance with the present invention are set out below.

|   | Range |
| --- | --- |
| a) Sorbitan sesqui-isostearate | 3 to 20% |
| Preservative | 0.1 to 1% |
| Gelled mineral oil (e.g. | |

-continued

|  | Range |
|---|---|
| Plastibase 50W, Squibb) | 75 to 95% |
| b) Triglyceryl di-isostearate | 3 to 20% |
| Preservative | 0.1 to 1% |
| Gelled mineral oil (e.g. Plastibase 50W, Squibb) | 75 to 95% |

Examples of preferred water-in-oil cream bases in accordance with the present invention are set out below.

|  | Range |
|---|---|
| a) Sorbitan sesqui-isostearate | 1 to 20% |
| Preservative | 0.1 to .5% |
| Gelled mineral oil (e.g. Plastibase 50W, Squibb | 5 to 90% |
| Water | 5 to 90% |
| b) Triglyceryl di-isostearate | 1 to 20% |
| Preservative | 0.1 to 0.5% |
| Gelled mineral oil (e.g. Plastibase 50W, Squibb) | 5 to 90% |
| Water | 5 to 90% |
| In the above, Plastibase 50W, Squibb refers to mineral oil gelled with 5% polyethylene. |  |
| c) Sorbitan sesqui-isostearate | 1 to 20% |
| Hexadecyl alcohol | 60 to 85% |
| High Melting Waxes (m.p. 137°-139° C. - Acrawax C - Glyco Products) | 7 to 15% |
| High molecular weight fatty acids ($C_{29}$ and higher, m.p. 67°-73° C., Emery 865-A) | 2 to 8% |
| Butylene glycol distearate | 3 to 8% |

The ointment bases of the invention will withstand elevated temperatures of a minimum of 50° and even up to 90° C. depending upon the melting point of the lipophilic gelling agent and thus will not become rancid on storage at such temperatures. They possess high water absorbency, for example, up to two to ten times or more of its weight depending on the amount of water-in-oil emulsifier used, will adhere to dry or wet surfaces, such as oral, eye or wet skin for medicinal uses. They are non-irritating, hypo-allergic or non-sensitizing, non-toxic, colorless, odorless and tasteless. Relatively large amounts of insoluble powders may be introduced into the base to make ointments without affecting the consistency of the ointment.

Normally, ointments or creams are considered satisfactory if their consistency does not change appreciably at 40° to 45° C. However, storage of such ointments in tropical countries has been a problem. Moreover, the bases of the present invention including ointments and creams are particularly suited for use in tropical countries because of their relatively good stability on storage at tropical temperatures.

The ointments and creams of the invention may be used as carriers for medicaments, such as antibodies, anti-bacterial agents, anti-fungal agents, dental products, antihistamines, and the like.

The following Examples illustrate preferred embodiments of the invention.

EXAMPLE 1

An absorption ointment of the following composition is prepared as described below.

| Sorbitan sesqui-isostearate | 6.0 gm. |
|---|---|
| Methylparaben, U.S.P. | 0.5 gm. |
| Mineral oil gelled with 5% polyethylene (Plastibase 50W, Squibb) | 93.5 gm. |

The sorbitan sesqui-isostearate and methylparaben are mixed with the Plastibase 50W in a planetary type mixer and blended until homogeneous.

EXAMPLE 2

An absorption ointment of the following composition is prepared as described below.

| Triglyceryl di-isostearate | 6.0 gm. |
|---|---|
| Methylparaben, U.S.P. | 0.5 gm. |
| Mineral oil gelled with 5% polyethylene (Plastibase 50W, Squibb) | 93.5 gm |

The triglyceryl di-isostearate and methylparaben are mixed with the Plastibase 50W in a planetary type mixer and blended until homogeneous.

EXAMPLE 3

A high temperature stable water-in-oil cream of the following composition is prepared as described below.

| Sorbitan sesqui-isostearate | 3.0 gm. |
|---|---|
| Methylparaben, U.S.P. | 0.2 gm. |
| Mineral oil gelled with 5% polyethylene (Plastibase 50W, Squibb) | 20 gm. |
| Purified water, q.s. | 100.0 gm. |

The sorbitan sesqui-isostearate and methylparaben are mixed with the Plastibase 50W and water in a planetary type mixer and blended until homogeneous.

EXAMPLE 4

A high temperature stable water-in-oil cream of the following composition is prepared as described below.

| Triglyceryl di-isostearate | 3.0 gm. |
|---|---|
| Methylparaben, U.S.P. | 0.1 gm. |
| Mineral oil gelled with 5% polyethylene (Plastibase 50W, Squibb) | 20 gm. |
| Purified Water q.s. | 100 gm. |

The triglyceryl di-isostearate and methylparaben are mixed with the Plastibase 50W and water in a planetary type mixer and blended until homogeneous.

EXAMPLES 5 to 9

Absorption creams of the following compositions are prepared as described below.

|  | Example No. | | |
|---|---|---|---|
|  | 5 | 6 | 7 |
| Sorbitan triisostearate (Emsorb 2519) | 2 gm | 3 gm | 4 gm |
| Mineral oil gelled with 5% polyethylene (Plastibase 50W, Squibb) | 98 gm | 97 gm | 96 gm |

|  | Example No. | |

-continued

| | 8 | 9 |
|---|---|---|
| Sorbitan triisostearate (Emsorb 2519) | 5 gm | 6 gm |
| Mineral oil gelled with 5% polyethylene (Plastibase 50W, Squibb) | 95 gm | 94 gm |

The sorbitan triisostearate is added to 25 g Plastibase 50W and mixed therein. The resulting mixture is added to the remainder of the Plastibase 50W and mixed therewith. Thereafter, 100 g water is mixed therewith to form an absorption cream.

EXAMPLE 10

Neomycin Sulfate Water-in-Oil Cream

A neomycin sulfate water-in-oil cream having the following formulation is prepared as described below.

| Neomycin sulfate | 0.3 gm. |
|---|---|
| Methylparaben | 0.2 gm. |
| Triglyceryl diisostearate | 4.0 gm. |
| Mineral oil gelled with 5% polyethylene (Plastibase 50W, Squibb) | 20.0 gm. |
| Distilled water q.s. | 100.0 gm. |

The neomycin sulfate is dissolved in 90 ml distilled water. Methylparaben is added and mixed into the neomycin sulfate mixture.

The triglyceryl diisostearate is thoroughly mixed with the Plastibase 50W to form the ointment. Thereafter, approximately 30 ml portions of the above neomycin sulfate aqueous solution is incorporated into the ointment until the ointment is emulsified. About 4.5 ml of distilled water is then mixed into the ointment to form a cream.

EXAMPLE 11

Dental Ointment

A dental ointment having the following formulation is prepared in a manner similar to that described in Example 10 with the exception that strontium chloride and sorbitan sesqui-isostearate are employed in place of neomycin sulfate and triglyceryl diisostearate.

| Strontium chloride | 2.0 gm. |
|---|---|
| Sorbitan sesqui-isostearate | 5.0 gm. |
| Methylparaben | 0.2 gm. |
| Mineral oil gelled with 5% polyethylene (Plastibase 50W, Squibb) | 20.0 gm. |
| Distilled water q.s. | 100.0 gm. |

EXAMPLE 12

Anti-Bacterial Cream

An anti-bacterial cream having the following formulation is prepared as described in Example 10 except that chlorhydroxyquinoline is employed in place of neomycin sulfate and methyl paraben.

| Chlorhydroxyquinoline | 2.0 gm. |
|---|---|
| Triglyceryl diisostearate | 4.0 gm. |
| Mineral oil gelled with 5% polyethylene (Plastibase 50W, Squibb) | 20.0 gm. |
| Distilled water q.s. | 100.0 gm. |

EXAMPLE 13

Antibiotic Cream

An antibiotic cream having the following formulation is prepared as described in Example 10 except that chloramphenicol is employed in place of neomycin sulfate.

| Chloramphenical | 2.0 gm. |
|---|---|
| Triglyceryl diisostearate | 4.0 gm. |
| Methylparaben | 0.2 gm. |
| Mineral oil gelled with 5% polyethylene (Plastibase 50W, Squibb) | 20.0 gm. |
| Distilled water q.s. | 100.0 gm. |

EXAMPLE 14

Anti-fungal Cream

An anti-fungal cream having the following formulation is prepared as described in Example 10 except that zinc undecylenate is employed in place of neomycin sulfate.

| Zinc Undecylenate | 3.0 gm. |
|---|---|
| Triglyceryl diisostearate | 4.0 gm. |
| Methylparaben | 0.2 gm. |
| Mineral oil gelled with 5% polyethylene (Plastibase 50W, Squibb) | 20.0 gm. |
| Distilled water q.s. | 100.0 gm. |

EXAMPLE 15

Skin-whitening Cream

A skin-whitening cream having the following formulation is prepared as described in Example 10 except that hydroquinone and sorbitan sesqui-isostearate are employed in place of neomycin sulfate and triglyceryl diisostearate.

| Hydroquinone | 2.0 gm. |
|---|---|
| Sorbitan sesqui-isostearate | 5.0 gm. |
| Methylparaben | 0.2 gm. |
| Mineral oil gelled with 5% polyethylene (Plastibase 50W, Squibb) | 20.0 gm. |
| Distilled water q.s. | 100.0 gm. |

It will also be appreciated that medicinal ointments may be formed containing any of the active ingredients of Examples 10 to 15. In such case, the active ingredient will be simply blended with ointment formulations as described hereinbefore.

What is claimed is:

1. A gelled mineral oil vehicle for medicinals said vehicle having improved high temperature stability and water-absorption properties, comprising a gelled mineral oil and containing a water absorption promoter comprising an oily liquid at room temperature and free of unsaturated fatty acid moiety, and which is a member selected from the group consisting of triglyceryl diisostearate, sorbitan sesqui-isostearate, sorbitan triisostearate, polyethylene glycol isostearyl ether, polyethylene glycol diisostearyl ether, and mixtures thereof, said vehicle being stable at temperatures of 80° C. or higher, without becoming rancid, and being capable of absorbing 2 to 10 times its weight in water.

2. The vehicle as defined in claim 1 wherein said promotor is selected from the group consisting of sorbitan sesqui-isostearate, triglyceryl diisostearate, sorbitan triisostearate, and mixtures thereof.

3. The vehicle as defined in claim 1 wherein said promoter is selected from the group consisting of polyethylene glycol isostearyl ether, polyethylene glycol diisostearyl ether, and mixtures thereof.

4. The vehicle as defined in claim 1 wherein said promoter is present in an amount at least about 0.5% by weight of the vehicle.

5. The vehicle as defined in claim 4 wherein said promoter is employed in an amount within the range of from about 1 to about 30% by weight of the vehicle.

6. The vehicle as defined in claim 1 in the form of an ointment.

7. The vehicle as defined in claim 1 in the form of a water-in-oil cream.

8. The vehicle as defined in claim 1 wherein said gelled mineral oil is gelled with polyethylene.

9. A method for preparing the vehicle as defined in claim 1, which comprises mixing at room temperature a gelled mineral oil with a water absorption promoter comprising an oily liquid at room temperature and free of unsaturated fatty acid moiety and which is a member selected from the group consisting of triglyceryl diisostearate, sorbitan sesqui-isostearate, and sorbitan triisostearate.

10. The method as defined in claim 9 further including the step of adding water to form a water-in-oil cream.

11. A method for improving high temperature stability and water absorption properties of gelled mineral oil, which comprises admixing gelled mineral oil with a water absorption promoter comprising an oily liquid at room temperature and free of unsaturated fatty acid moiety, and which is a member selected from the group consisting of triglyceryl diisostearate, sorbitan sesqui-isostearate, sorbitan triisostearate, polyethylene glycol isostearyl ether, polyethylene glycol diisostearyl ether, and mixtures thereof, said gelled mineral oil being stable at temperatures of 80° C. or higher, without becoming rancid, and being capable of absorbing 2 to 10 times its weight in water.

* * * * *